United States Patent
Jin et al.

(10) Patent No.: US 11,692,204 B2
(45) Date of Patent: *Jul. 4, 2023

(54) USE OF GENOMIC NW_006880285.1 IN CHO CELL FOR STABLY EXPRESSING A PROTEIN

(71) Applicant: Jiangnan University, Wuxi (CN)

(72) Inventors: Jian Jin, Wuxi (CN); Yun Chen, Wuxi (CN); Huazhong Li, Wuxi (CN); Songtao Zhou, Wuxi (CN); Zuoying Duan, Wuxi (CN); Xiaohai Gong, Wuxi (CN)

(73) Assignee: JIANGNAN UNIVERSITY, Wuxi (CN)

( * ) Notice: Subject to any disclaimer, the term of this patent is extended or adjusted under 35 U.S.C. 154(b) by 464 days.

This patent is subject to a terminal disclaimer.

(21) Appl. No.: 16/644,953

(22) PCT Filed: Dec. 3, 2018

(86) PCT No.: PCT/CN2018/118887
§ 371 (c)(1),
(2) Date: Mar. 5, 2020

(87) PCT Pub. No.: WO2020/087640
PCT Pub. Date: May 7, 2020

(65) Prior Publication Data
US 2021/0222202 A1    Jul. 22, 2021

(30) Foreign Application Priority Data
Oct. 30, 2018   (CN) .......................... 201811274680.0

(51) Int. Cl.
*C12N 15/90*   (2006.01)
*C12N 15/66*   (2006.01)

(52) U.S. Cl.
CPC ............ *C12N 15/907* (2013.01); *C12N 15/66* (2013.01); *C12N 2310/20* (2017.05); *C12N 2510/02* (2013.01); *C12N 2800/80* (2013.01)

(58) Field of Classification Search
CPC .. C12N 15/907; C12N 15/66; C12N 2310/20; C12N 2510/02; C12N 2800/80; C12N 5/0682; C12N 15/85
See application file for complete search history.

(56) References Cited

FOREIGN PATENT DOCUMENTS

| CN | 107557390 A | * | 1/2018 |
|---|---|---|---|
| KR | 20180031875 A | | 3/2018 |
| WO | 2008079943 A2 | | 7/2008 |

OTHER PUBLICATIONS

U.S. Appl. No. 16/645,955, filed Mar. 2020, Li et al.*
Liu Xia, et al., Construction of Recombinant Human Thrombin Eukaryotic Expression Vector and Its Stable Expressior in CHO Cells, Food and Drug, 2013, pp. 381-384, 15, 6.
Liu Xia, et al., Construction of Eukaryotic Expression Vector of Human Hyaluronidase and Establishment of Its Stable Transfected CHO Cell Line, Food and Drug, 2013, pp. 80-83, 15, 2.
Yuan Chengfu, et al., Construction of eukaryotic expression vector of human MCHR2 and establishment of its stable transfected CHO cell line, Acta Academiae Medicinae Militarist Tertial, Jan. 2007, pp. 32-35, vol. 29, No. 1.

* cited by examiner

*Primary Examiner* — Iqbal H Chowdhury
(74) *Attorney, Agent, or Firm* — Bayramoglu Law Offices LLC

(57) ABSTRACT

Use of genomic NW_006880285.1 in CHO cell for stably expressing a protein is disclosed. The certain site in CHO cell genome for stably expressing a protein is positioned at a base of No. 1235357 in a CHO cell gene NW_006880285.1; a sequence of 5' NNNNNNNNNNNNNNNNNNNNNGG3' that can be identified by CRISPR/Cas9 technology and positioned in a base range of No. 1235284-1235429 around the certain site is a target sequence. Various of protein genes are introduced into a fixed site in CHO cell genome, and expressed stably in the present disclosure.

13 Claims, 2 Drawing Sheets

Specification includes a Sequence Listing.

SEQUENCE LISTING

<160> NUMBER OF SEQ ID NOS: 15

<210> SEQ ID NO 1
<211> LENGTH: 23
<212> TYPE: DNA
<213> ORGANISM: Cricetulus griseus

<400> SEQUENCE: 1
gaaagaaggt ctgatatcaa agg                           23

<210> SEQ ID NO 2
<211> LENGTH: 23

```
<212> TYPE: DNA
<213> ORGANISM: Cricetulus griseus

<400> SEQUENCE: 2
aaagaaggtc tgatatcaaa ggg                                            23

<210> SEQ ID NO 3
<211> LENGTH: 23
<212> TYPE: DNA
<213> ORGANISM: Cricetulus griseus

<400> SEQUENCE: 3
cctcactagt acacgcacca tgg                                            23

<210> SEQ ID NO 4
<211> LENGTH: 23
<212> TYPE: DNA
<213> ORGANISM: Cricetulus griseus

<400> SEQUENCE: 4
tagcttgctc acagtagcac agg                                            23

<210> SEQ ID NO 5
<211> LENGTH: 23
<212> TYPE: DNA
<213> ORGANISM: Cricetulus griseus

<400> SEQUENCE: 5
cttgctcaca gtagcacagg agg                                            23

<210> SEQ ID NO 6
<211> LENGTH: 23
<212> TYPE: DNA
<213> ORGANISM: Cricetulus griseus

<400> SEQUENCE: 6
gctcacagta gcacaggagg agg                                            23

<210> SEQ ID NO 7
<211> LENGTH: 23
<212> TYPE: DNA
<213> ORGANISM: Cricetulus griseus

<400> SEQUENCE: 7
ctcacagtag cacaggagga ggg                                            23

<210> SEQ ID NO 8
<211> LENGTH: 23
<212> TYPE: DNA
<213> ORGANISM: Cricetulus griseus

<400> SEQUENCE: 8
gcaagctaca tagttaccca tgg                                            23

<210> SEQ ID NO 9
<211> LENGTH: 23
<212> TYPE: DNA
<213> ORGANISM: Cricetulus griseus

<400> SEQUENCE: 9
ccatggtgcg tgtactagtg agg                                            23

<210> SEQ ID NO 10
```

```
<211> LENGTH: 23
<212> TYPE: DNA
<213> ORGANISM: Cricetulus griseus

<400> SEQUENCE: 10 caactttag ctacattcct tgg                                              23

<210> SEQ ID NO 11
<211> LENGTH: 23
<212> TYPE: DNA
<213> ORGANISM: Cricetulus griseus

<400> SEQUENCE: 11
aggaatgtag ctaaaagttg agg                                             23

<210> SEQ ID NO 12
<211> LENGTH: 145
<212> TYPE: DNA
<213> ORGANISM: Artificial Sequence
<220> FEATURE:
<223> OTHER INFORMATION: Synthetic DNA

<400> SEQUENCE: 12
cctcctcctg tgctactgtg agcaagctac atagttaccc atggtgcgtg tactagtgag     60
gtgattgatt gacagactag tagaagcaca cacctcaact tttagctaca ttccttggtc    120
tccctttgat atcagacctt ctttc                                          145

<210> SEQ ID NO 13
<211> LENGTH: 26
<212> TYPE: DNA
<213> ORGANISM: Artificial Sequence
<220> FEATURE:
<223> OTHER INFORMATION: Synthetic DNA

<400> SEQUENCE: 13
tttggaaaga aggtctgata tcaagt                                          26

<210> SEQ ID NO 14
<211> LENGTH: 26
<212> TYPE: DNA
<213> ORGANISM: Artificial Sequence
<220> FEATURE:
<223> OTHER INFORMATION: Synthetic DNA

<400> SEQUENCE: 14
taaaacttga tatcagacct tctttc                                          26

<210> SEQ ID NO 15
<211> LENGTH: 23
<212> TYPE: DNA
<213> ORGANISM: Cricetulus griseus
<220> FEATURE:
<221> NAME/KEY: misc_feature
<222> LOCATION: (1)..(21)
<223> OTHER INFORMATION: n is a, c, g, or t

<400> SEQUENCE: 15
nnnnnnnnnn nnnnnnnnnn ngg                                             23
```

USE OF GENOMIC NW_006880285.1 IN CHO CELL FOR STABLY EXPRESSING A PROTEIN

CROSS REFERENCE TO THE RELATED APPLICATIONS

This application is the national phase entry of International Application No. PCT/CN2018/118887, filed on Dec. 3, 2018, which is based upon and claims priority to Chinese Patent Application No. 201811274680.0, filed on Oct. 30, 2018, the entire contents of which are incorporated herein by reference.

SEQUENCE LISTING

The instant application contains a Sequence Listing which has been submitted in ASCII format via EFS-Web and is hereby incorporated in its entirety. Said ASCII copy is named GBHY033_ST252.txt, created on 8/10/2022, and is 2,992 bytes in size.

TECHNICAL FIELD

The present disclosure relates to the field of gene technology, particularly to gene recombination in a CHO cell for stably expressing a protein.

BACKGROUND

Chinese Hamster Ovary (CHO) cell is an important cell line used in biopharmaceuticals. Many different types of CHO cell lines have been developed including a cell line that can be used to expand gene copy numbers. However, by increasing transgene copy number is not correlated well with the increase in express level of the target protein. Also, the expression level of most CHO cells is unstable even with increased protein expression. The current mostly used method of constructing stable transfected cells is time-consuming and labor-intensive, mainly due to repetitive monoclonal screening processes. Thus, it is currently expected in the field of cell line construction that a method of obtaining a cell expressed stably and in a high level within a short time, and can ensure that the constructed recombinant cell line has the same quality level as traditional methods to ensure regulatory approval.

A traditional method of constructing an exogenous protein-expressing cell line is to randomly integrate an exogenous gene into the cell genome, which is subjected to screening of a series of high-expressing monoclonal cells, to obtain a cell line with a high expressing of exogenous protein. Due to the diversity of site effect differences, the recombinant cells produced by random integration have different expression levels. It takes a long time and many steps to select high-expressing monoclonal cells. Monoclonal cells obtained through random integration cannot guarantee stably expressing peptides/proteins in cell passages, and monoclonal screening needs to be repeated at each time a recombinant cell is constructed, increasing the cost of research and development of biopharmaceuticals.

The site effect hinders the efficiency of traditional random integration to construct recombinant cell lines. Repetitive high-expression monoclonal screening is time-consuming, labor-intensive and expensive. How to overcome the site effect and to obtain quickly and efficiently stable expressing monoclonal cells by using the site-specific integration technology has been discussed in the art for many years, and there has been no breakthrough progress.

SUMMARY

In view of the above problems in the prior art, the applicant of the present disclosure provides use of a certain site in CHO cell genome for stably expressing a protein. In the present disclosure, different protein genes are introduced into the CHO cell genome at a fixed position and expressed stably. In addition, in the process of achieving the site-specific integration, there is no need to select repeatedly monoclonal cells to obtain cell lines with higher expression, which saves a lot of time.

The technical solution of the present disclosure is as follows.

Use of a certain site in CHO cell genome for stably expressing a protein, wherein the certain site in CHO cell genome for stably expressing a protein is positioned at a base of No. 1235357 in a CHO cell gene NW_006880285.1; a sequence of 5' NNNNNNNNNNNN NNNNNNNNNGG3', as shown in SEQ ID NO: 15, and that can be identified by CRISPR/Cas9 technology and positioned in a base range of No. 1235284-1235429 around the certain site is a target sequence.

The protein has a molecular weight of less than 160 KDa.

The protein is one selected from the group consisting of polypeptide, a functional protein, an antibody, and a fusion protein.

The target sequence is the bases positioned at No. 1235285-1235307, upstream of the base of No. 1235357 in the CHO cell gene NW_0068802851 The target sequence is 5'-GAAAGAAGGTCTGATATCAAAGG-3', as shown in SEQ ID NO:1.

In a preferable embodiment, the target sequence is 5'-AAAGAAGGTCTGATATCAAAGGG-3', as shown in SEQ ID NO:2.

In a preferable embodiment, the target sequence is 5'-CCTCACTAGTACACGCACCATGG-3', as shown in SEQ ID NO:3.

In a preferable embodiment, the target sequence is 5'-TAGCTTGCTCACAGTAGCACAGG-3', as shown in SEQ ID NO:4.

In a preferable embodiment, the target sequence is 5'-CTTGCTCACAGTAGCACAGGAGG-3', as shown in SEQ ID NO:5.

In a preferable embodiment, the target sequence is 5'-GCTCACAGTAGCACAGGAGGAGG-3', as shown in SEQ ID NO:6.

In a preferable embodiment, the target sequence is 5'-CTCACAGTAGCACAGGAGGAGGG-3', as shown in SEQ ID NO:7.

In a preferable embodiment, the target sequence is 5'-GCAAGCTACATAGTTACCCATGG-3', as shown in SEQ ID NO:8.

In a preferable embodiment, the target sequence is 5'-CCATGGTGCGTGTACTAGTGAGG-3', as shown in SEQ ID NO:9.

In a preferable embodiment, the target sequence is 5'-CAACTTTTAGCTACATTCCTTGG-3', as shown in SEQ ID NO:10.

In a preferable embodiment, the target sequence is 5'-AGGAATGTAGCTAAAAGTTGAGG-3', as shown in SEQ ID NO:11.

The present disclosure provides a recombinant donor carrier containing the target sequence for expressing the protein.

The recombinant donor carrier is a carrier for CHO cell expression.

The recombinant donor carrier is prepared by inserting a protein gene into a region between the 5'arm and 3'arm of the plasmid, so that the nucleotide sequence is located downstream of the promoter and is regulated by the promoter to obtain a recombinant CHO cell expression plasmid.

The promoter is one selected from the group consisting of CMV (a strong promoter for expression in a mammalian cell derived from human cytomegalovirus), EF-1a (a strong promoter for expression in a mammalian cell derived from human elongation factor 1α), SV40 (a promoter for expression in a mammalian cell derived from simian vacuole virus 40), PGK1 (a promoter for expression in a mammalian cell derived from phosphoglycerate kinase gene), UBC (a promoter for expression in a mammalian cell derived from human ubiquitin C gene), human beta actin (a promoter for expression in a mammalian cell derived from β-actin gene), and CAG (a strong hybrid promoter for expression in a mammalian cell).

Also provided is a recombinant CHO cell line for stably expressing a protein.

Further provided is a method for expressing a protein by a gene in a CHO cell including (1) transforming a CHO cell with a recombinant donor carrier to obtain a recombinant CHO cell;

(2) culturing the recombinant CHO cell on a plate, and collecting the supernatant to detect the expression level, and adapting an adherent recombinant CHO cell to suspension culture;

(3) culturing the adopted recombinant CHO cell in a shake flask and determining the protein expressing level.

The present disclosure also provides a selection of a stable expression site in a CHO cell genome 1) constructing a lentivirus with a fluorescent label and calculating its titer; integrating igk-luc gene to a multiple cloning site on pLVX-CMV-MCS-T2A-Zsgreen carrier, followed by performing three plasmid transfection to HEK-293T cell by using plasmids of pSPAX2 and pMD2G, aspirating the supernatant twice at 48 h and 72 h, ultracentrifuging the supernatant to obtain lentivirus;

2) placing the CHO cells on a 6-well plate and culturing the CHO cells overnight, diluting the lentivirus on the following day, infecting the CHO cells at a low MOI (multiplicity of infection) (MOI<1)(number of virus particles corresponding to each cell); sorting the cells with a flow cell sorter after 96 hrs from the infection, and inoculating the cells with the highest fluorescence intensity directly into a 96-well plate; culturing continuously for one week so that the cells grow into monoclonal colonies; observing the CHO cells with a fluorescent microscope, marking the brightest colonies having a normal morphology, and transferring the cells to a 24-well plate for expansion upon achieving a desired cell number; transferring the cells to a 6-well plate when a confluence of nearly 90% is achieved, and finally transferring to a 10 cm culture dish; and freezing part of the cells and expanding the remaining cells;

3) searching out all gene integration sites of CHO cells in lentivirus with chromosome walking technology by using Lenti-X Integration Site Analysis Kit (Clontech: 631263).

Genomic DNA was digested overnight with three restriction enzymes: ADraI, SspI, and HpaI, by using several cell lines with the highest fluorescence intensity and normal cell morphology and growth rate as material. A reaction system of 100 μL was prepared with 2.5 μg of genomic DNA and 80 U of restriction enzyme, and was digested at 37° C. overnight (16-18 hours).

The digested product was purified and recovered with a DNA recovery kit. A ligation system for test was prepared with 4.8 μL of the digested genomic DNA, 1.9 μL of genome walker adaptor (25 μM) and 0.5 μL of T4 ligase, which is placed at 16° C. for ligation overnight. The ligation system was heated at 70° C. for 5 minutes to inactivate the ligase. 32 μL of TE buffer was added to each system to prepare corresponding library.

Two rounds of nested PCR were performed on the library to amplify the LTR region and adjacent genomic regions. Related steps for PCR reaction can be referred to the instructions of Lenti-X Integration Site Analysis Kit (Clontech: 631263) kit.

Finally, the PCR products were electrophoresed, and the main bands were cut and recovered for sequencing. After obtaining all the lentiviral integration information of each cell line, the relevant information of the CHO cell line with only a single copy of the lentivirus integration was select, and compared with the CHO-K1 genome information on BLAST to find out the integration site with high expression.

The present disclosure has the following advantages:

A site-specific integration method is used in the present application to integrate the target gene into a stable expression region at a specific site. The method can well address the problem of uncertain integration site caused by random integration, and effectively avoid repetitive screening for high-expressing monoclonal cells. Therefore, the method can effectively reduce development time of biopharmaceuticals to build stable expression cell lines, and thus reduce costs.

In the present disclosure, a protein gene is introduced at a fixed site of a CHO cell gene and stably expressed.

DETAILED DESCRIPTION

The present disclosure is described in detail below with reference to the drawings and embodiments.

Figure 1:
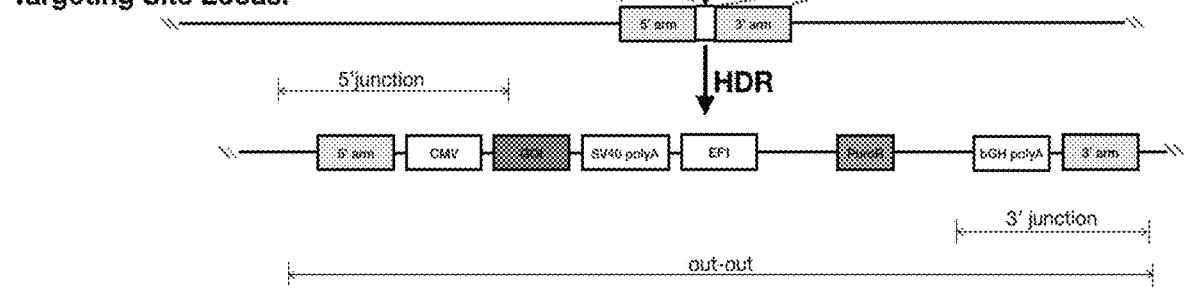
FIG. 1 shows a schematic diagram of the present disclosure.

FIG. 1 is a schematic diagram of a donor plasmid for integration to the site and a simulated schematic diagram of how to integrate to the site by homologous recombination. GOI as a target gene is integrated to a target site via two homologous recombination arms of 5'arm and 3'arm under a puromycin screening concentration of 4 μg/mL. In addition, the sequence upstream of 5'arm as a negative mark of screening can be used to remove monoclonal cells that are randomly integrated, such that recombinant CHO cells that are integrated at a specific site can be finally recovered.

Example 1

Selection of High Expression Site

Zsgreen1 gene was integrated at the base of No. 1235357 in NW_006880285.1 gene of a cell. The obtained fluorescence cell was cultured for no less than 50 passages. The expression level was detected with a flow cytometry. The 50th generation of fluorescent cells still had a good green fluorescent protein expression level. The fluorescent signal was stably retained during the passage of the cells.

In addition, this fluorescent cell was also adapted to suspension, and the expression level of the fluorescent protein after adaption was detected again with a flow cytometry. The results show that among the recombinant CHO cells that are suspended over 50 passages, more than 95% maintains the expression level of the green fluorescent protein after suspension. It can be seen that the site is very stable and the fluorescent protein gene will not be lost due to passage of the cells.

Example 2

Selection of a Specific Target Sequence

According to proximity principle, the sequence of

5'CCTCCTCCTGTGCTACTGTGAGCAAGCTACATAGTTACCCATGGTGCG

TGTACTAGTGAGGTGATTGATTGACAGACTAGTAGAAGCACACACCTCAA

CTTTTAGCTACATTCCTTGGTCTCCCTTTGATATCAGACCTTCTTTC 3' as shown in SEQ ID NO: 12, was input into CRISRPRater System, and a target sequence with low off-target rate was predict and select. The parameter settings are as follows: 1) the maximum number of mismatched bases of the first 15 base pairs (bps) after NGG is 0; 2) the number of mismatched bases of all 21 bps after NGG is 2.

According to the above operation, the following sequence with a score of 0.72 is selected as the target sequence:

5'-GAAAGAAGGTCTGATATCAAAGG-3', SEQ ID NO: 1; and according to the CRISPRater System, LOW efficacy (score<0.56); MEDIUM efficacy (0.56<=score<=0.74); and HIGH efficacy (score>0.74).

According to the CRISPRater System, all target sequences in the range of 1235284-1235429 near NW_006880285.1 have scores above 0.56, all of which are in the range of moderate or highly effective, and can be used as 5' NNNNNNNNNNNNNNNNNNNNNGG3', SEQ ID NO: 15, target sequence that can be identified by CRISPR/Cas9 technology.

Example 3 Selection of Promoters

The promoter of CMV (a strong promoter for expression in a mammalian cell derived from human cytomegalovirus) is replaced with various promoters including common promoters such as EF-1a (a strong promoter for expression in a mammalian cell derived from human elongation factor 1α), SV40 (a promoter for expression in a mammalian cell derived from simian vacuole virus 40), PGK1 (a promoter for expression in a mammalian cell derived from phosphoglycerate kinase gene), UBC (a promoter for expression in a mammalian cell derived from human ubiquitin C gene), human beta actin (a promoter for expression in a mammalian cell derived from β-actin gene), and CAG (a strong hybrid promoter for expression in a mammalian cell). It is determined by testing that the above promoters can regulate the downstream human serum albumin (HSA) gene sequence and express the corresponding HSA protein.

Example 4

The human serum albumin gene (HSA, 68 KDa) is integrated at a specific site. For homologous recombination mediated by CRISPR/Cas9 later, sgRNA and donor plasmid were required to be constructed as follows.

1. First the following sequence was synthesized for construction of SgRNA:

sgRNA-1fwd 5' TTTG GAAAGAAGGTCTGATATCAA GT 3', as shown in SEQ ID NO:13, and sgRNA-1rev 5' TAAAACTTGATATCA-GACCTTCTTTC 3', as shown in SEQ ID NO:14.

1) The plasmid of PSK-u6-gRNA was digested with BBsI enzyme, and the resulted carriers were recovered;

2) synthetic fragments were annealed into double strands with sticky ends:

sgRNA-1fwd (100 μM) 4 μL
sgRNA-1rev (100 μM)
10×NEB buffer2 2 μL
H$_2$O 10 μL
20 μL by treated in a water bath at 95° C. for 5 min, and then naturally cooled to room temperature;

3) the fragments were joint and recombinant plasmids were constructed recycled linear carriers 50 ng
annealed segments 1 μL
10×T4 ligase buffer 1 μL
T4 ligase 1 μL
H$_2$O
to 10 μL;

4) joining and conversion; and 5) cloning cells were selected and subjected to PCR identification, and the primer used for identification is M13-Synthetic primer R; those showing bands were identified as positive clones.

2. Construction of donor plasmid

The donor plasmid is described in FIG. 1 in details: segments expect for GOI were synthesized; the sequence of 600 bps upstream and downstream of the target sequence is the sequence information of the left and right homology arms of the donor plasmid. The GOI is obtained by integrating HSA onto the donor plasmid with the existing C115 kit from Vazyme Biotech.

3. Cas9 (donated by Dr. Helene F Kildegaard from Technical University of Denmark), SgRNA and donor plasmid with a molar ratio of 1:1:1 were co-transfected into CHO cells cultured at 37° C. with 5% CO$_2$, and transfection reagent is Lipofectamine 3000 (Thermo Fisher Scientific). The method of transfection can be referred to instructions from the supplier. 4 μg/mL puromycin was then added into the resulted cells for screening for 10 days. MoFloXDP FACS machine (Beckman Coulter) was used to monoclonal cell sorting. Cells without any fluorescence are selected and inoculated into a 96-well plate.

4. After 2 weeks of growth, part of the cells was taken for identification with 5' junction PCR, 3'Junction PCR and out-out PCR, and keep positive cells.

Example 5

The glucagon-like peptide-1-human serum albumin fusion protein gene (NGGH, 75 KDa) was integrate at a specific site. In order to construct CRISPR/Cas9-mediated homologous recombination at a later stage, sgRNA and Donor Plasmid need to be constructed as below.

1. SgRNA was constructed as in example 4.
2. Construction of donor plasmid

The donor plasmid is described in FIG. 1 in details: segments expect for GOI were synthesized; the sequence of 600 bps upstream and downstream of the target sequence is the sequence information of the left and right homology arms of the donor plasmid. The GOI is obtained by integrating HSA onto the donor plasmid with the existing C115 kit from Vazyme Biotech.

3. Cas9 (donated by Dr. Helene F Kildegaard from Technical University of Denmark), SgRNA and donor plasmid with a molar ratio of 1:1:1 were co-transfected into CHO cells cultured at 37° C. with 5% $CO_2$, and transfection reagent is Lipofectamine 3000 (Thermo Fisher Scientific). The method of transfection can be referred to instructions from the supplier. 4 μg/mL puromycin was then added into the resulted cells for screening for 10 days. MoFloXDP FACS machine (Beckman Coulter) was used to monoclonal cell sorting. Cells without any fluorescence are selected and inoculated into a 96-well plate.

4. After 2 weeks of growth, part of the cells was taken for identification with 5' junction PCR, 3'Junction PCR and out-out PCR, and keep positive cells.

Figure 2:
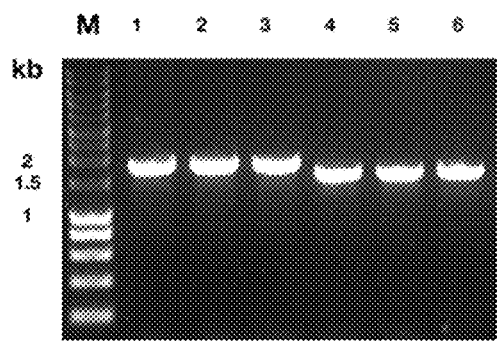
FIG. 2 shows the gene identification results of the CHO cells that NGGH 75 Kda gene is introduced thereinto.

FIG. 2 shows the gene identification results of the CHO cells with NGGH 75 KDa gene, wherein Lanes 1-3 are the 5'junction PCR results of three monoclonal cells, and Lanes 4-6 are the 3'junction PCR results, all of which have significant bands. It is confirmed that the target gene has been knocked-in.

Figure 3:
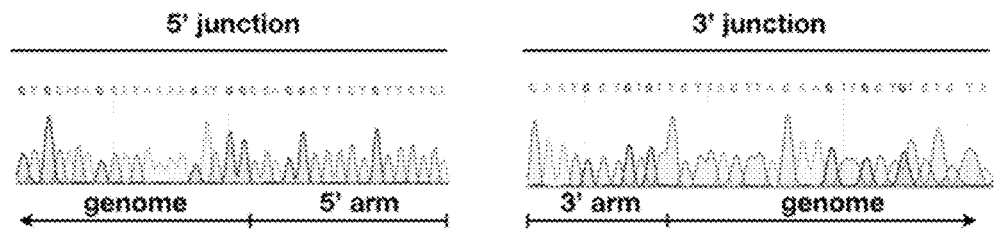
FIG. 3 shows the sequencing analysis of the CHO cells that NGGH 75 Kda gene is introduced thereinto with OoPCR_fwd and OoPCR_rev.

FIG. 3 shows sequencing with OoPCR_fwd and OoPCR_rev to determine that the sequence at the junction (the junction between the position upstream in the direction of 5' of 5' and 3'junctions and the genome) is accurate. The sequencing results verified that GOI was accurately inserted into the target region.

Example 6

The antibody gene (Avastin, 160 KDa) was integrated at a specific site. In order to construct CRISPR/Cas9-mediated homologous recombination at a later stage, sgRNA and Donor Plasmid need to be constructed as below.

1. SgRNA was constructed as in example 4.
2. Construction of donor plasmid

The donor plasmid is described in FIG. 1 in details: segments expect for GOI were synthesized; the sequence of 600 bps upstream and downstream of the target sequence is the sequence information of the left and right homology arms of the donor plasmid. The GOI is obtained by integrating Avastin onto the donor plasmid with the existing C115 kit from Vazyme Biotech.

3. Cas9 (donated by Dr. Helene F Kildegaard from Technical University of Denmark), SgRNA and donor plasmid with a molar ratio of 1:1:1 were co-transfected into CHO cells cultured at 37° C. with 5% $CO_2$, and transfection reagent is Lipofectamine 3000 (Thermo Fisher Scientific). The method of transfection can be referred to instructions from the supplier. 4 μg/mL puromycin was then added into the resulted cells for screening for 10 days. MoFloXDP FACS machine (Beckman Coulter) was used to monoclonal cell sorting. Cells without any fluorescence are selected and inoculated into a 96-well plate.

4. After 2 weeks of growth, part of the cells was taken for identification with 5' junction PCR, 3'Junction PCR and out-out PCR, and keep positive cells.

Testing Examples

The three cell lines prepared in Examples 4-6 were tested by ELISA to observe whether the protein of interest was expressed and whether it was stable long-term expression.

Detection method: all three tests were performed by ELISA method. All selected positive cells were cultured in a 6-well plate and tested for long-term stably expressing the target protein with kits of Human Albumin ELISA Kit (RK00157) and Human IgG(Total) ELISA Kit (RK00393).

Figure 4:
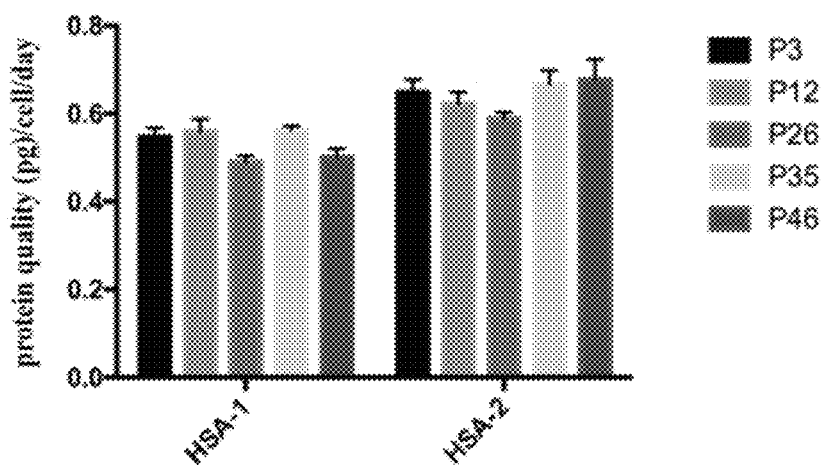
FIG. 4 shows the expression of HSA in cells in different passages.
Figure 5:
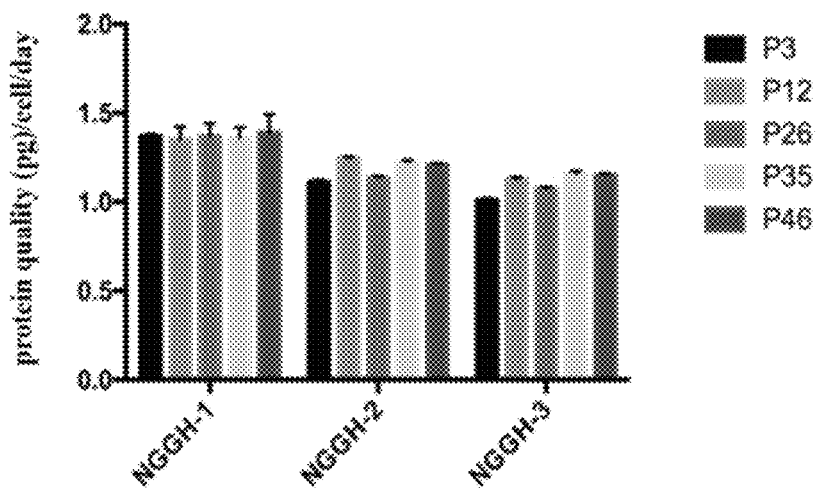
FIG. 5 shows the expression of NGGH in cells in different passages.

FIG. 4 and FIG. 5 show the expression of HSA and NGGH in cells at different passages, with the ordinate indicating the protein mass secreted in each cell daily.

It can be seen that NGGH and HSA can stably express the corresponding genes within 50 generations in the plate, and the selected protein expression levels of the 3 NGGH site-integrated cell lines and 2 HSA site-integrated cell lines are approaching.

Figure 6:
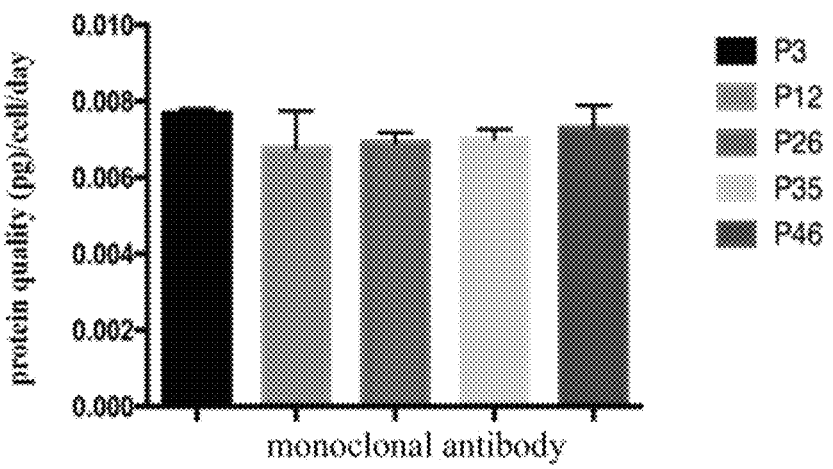
FIG. 6 shows the mass of antibody protein secreted by each recombinant CHO cell daily.

FIG. 6 shows the antibody protein mass secreted in each recombinant CHO cell daily. Obviously, the cells can stably express and secrete the corresponding proteins under different passage conditions, which shows good stability and is consistent with the previous results of fluorescent cells. The results show that this site can be used in CRISPR/Cas9-mediated site-specific integration and can stably express the corresponding protein.

Good results were obtained for the above test in which the 5'-GAAAGAAGGTCTGATATCAAAGG-3' sequence, SEQ ID NO: 1, is selected. Therefore, it shows that the target sequences in claims 5-14 can successfully construct a stable expression cell line by site-specific integration, and the protein of interest can be stably expressed for all cell lines.

What is claimed is:

1. A method for stably expressing a protein at a predetermined site in a Chinese hamster ovary (CHO) cell genome, wherein the predetermined site in the CHO cell genome for stably expressing the protein is positioned at a base of No. 1235357 in a CHO cell gene NW_006880285.1; the method comprises:
   identifying a nucleotide sequence of SEQ ID NO: 15 in a base range of No. 1235284-1235429 in the CHO cell gene NW_006880285.1, the base range having the nucleotide sequence of SEQ ID NO: 12, around the predetermined site by CRISPR/Cas9 technology as a target sequence,
   transforming the CHO cell with a recombinant donor carrier containing the target sequence to obtain a recombinant CHO cell;
   culturing the recombinant CHO cell and collecting the supernatant to detect the expression level, and adapting an adherent recombinant CHO cell to a suspension culture; and
   culturing the adapted recombinant CHO cell.

2. The method of claim 1, wherein the protein is one selected from the group consisting of a polypeptide, a functional protein, an antibody, and a fusion protein.

3. The method of claim 1, wherein the target sequence includes the bases positioned at No. 1235285-1235307 upstream of the base of No. 1235357 in the CHO cell gene NW_006880285.1, and the target sequence is the nucleotide sequence of SEQ ID NO:1.

4. The method of claim 1, wherein the target sequence is the nucleotide sequence of SEQ ID NO:2.

5. The method of claim 1, wherein the target sequence is the nucleotide sequence of SEQ ID NO:3.

6. The method of claim 1, wherein the target sequence is the nucleotide sequence of SEQ ID NO:4.

7. The method of claim 1, wherein the target sequence is the nucleotide sequence of SEQ ID NO:5.

8. The method of claim 1, wherein the target sequence is the nucleotide sequence of SEQ ID NO:6.

9. The method of claim 1, wherein the target sequence is the nucleotide sequence of SEQ ID NO:7.

10. The method of claim 1, wherein the target sequence is the nucleotide sequence of SEQ ID NO:8.

11. The method of claim 1, wherein the target sequence is the nucleotide sequence of SEQ ID NO:9.

12. The method of claim 1, wherein the target sequence is the nucleotide sequence of SEQ ID NO:10.

13. The method of claim 1, wherein the target sequence is the nucleotide sequence of SEQ ID NO:11.

* * * * *